United States Patent [19]
Manz

[11] Patent Number: 5,296,114
[45] Date of Patent: Mar. 22, 1994

[54] ELECTROPHORETIC SEPARATING DEVICE AND ELECTROPHORETIC SEPARATING METHOD

[75] Inventor: Andreas Manz, Bettingen, Switzerland

[73] Assignee: Ciba-Geigy Corporation, Ardsley, N.Y.

[21] Appl. No.: 983,178

[22] Filed: Nov. 30, 1992

[30] Foreign Application Priority Data

Dec. 6, 1991 [EP] European Pat. Off. ........ 91810952.1

[51] Int. Cl.⁵ .................... G01N 27/26; G01N 27/447
[52] U.S. Cl. ............................... 204/180.1; 204/299 R
[58] Field of Search ......................... 204/299 R, 180.1

[56] References Cited

U.S. PATENT DOCUMENTS 3,964,992  6/1976  Krotz ................................. 204/299
4,908,112  3/1990  Pace .................................. 204/299

FOREIGN PATENT DOCUMENTS 0376611  7/1990  European Pat. Off. .

OTHER PUBLICATIONS

Patent Abstract of Japan, vol. 13, No. 250, p. 882 (Shimadzu Corp.) Jun. 1989.
Patent Abstract of Japan, vol. 15, No. 347, Sep. 1991.
Journal of Chromatography, 456, (1988), 3–20.
Journal of High Resolution Chromatography, vol. 12, Dec. 1989, 797–801.

Primary Examiner—John Niebling
Assistant Examiner—John S. Starsiak, Jr.
Attorney, Agent, or Firm—Marla J. Mathias; William A. Teoli, Jr.

[57] ABSTRACT

In an electrophoretic separating device, a channel defining a separating path is constructed in the form of a closed loop. A sample to be separated is introduced via a feed opening into an electrolytic carrier medium that is moved with the aid of an electric field through the channel, which is provided in the region of its ends with inlet and outlet openings for the carrier medium, and is separated into individual components by the electric field. The electric field is generated in the channel by connecting electrodes in the region of the inlet and outlet openings to different potentials of a voltage source. The procedure for carrying out the method according to the invention is distinguished especially by the fact that the carrier medium and the sample are moved along the substantially closed separating path formed by the channel which is constructed in the form of a closed loop.

23 Claims, 4 Drawing Sheets

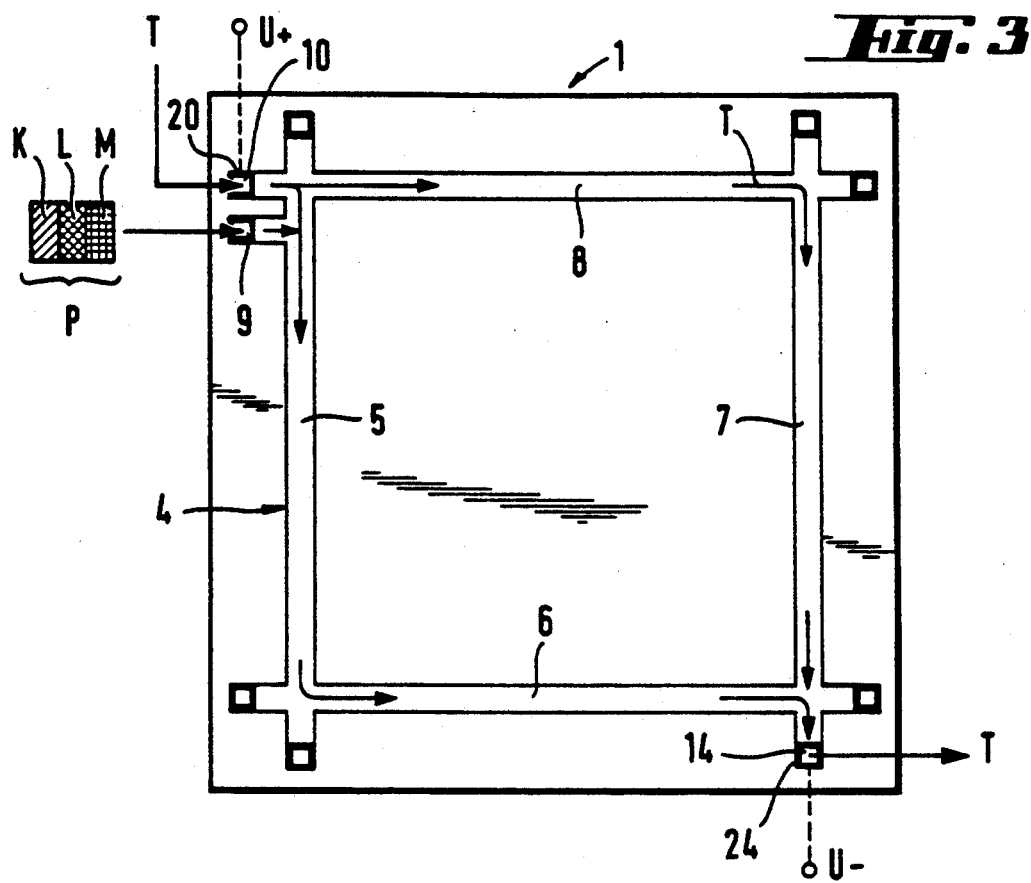
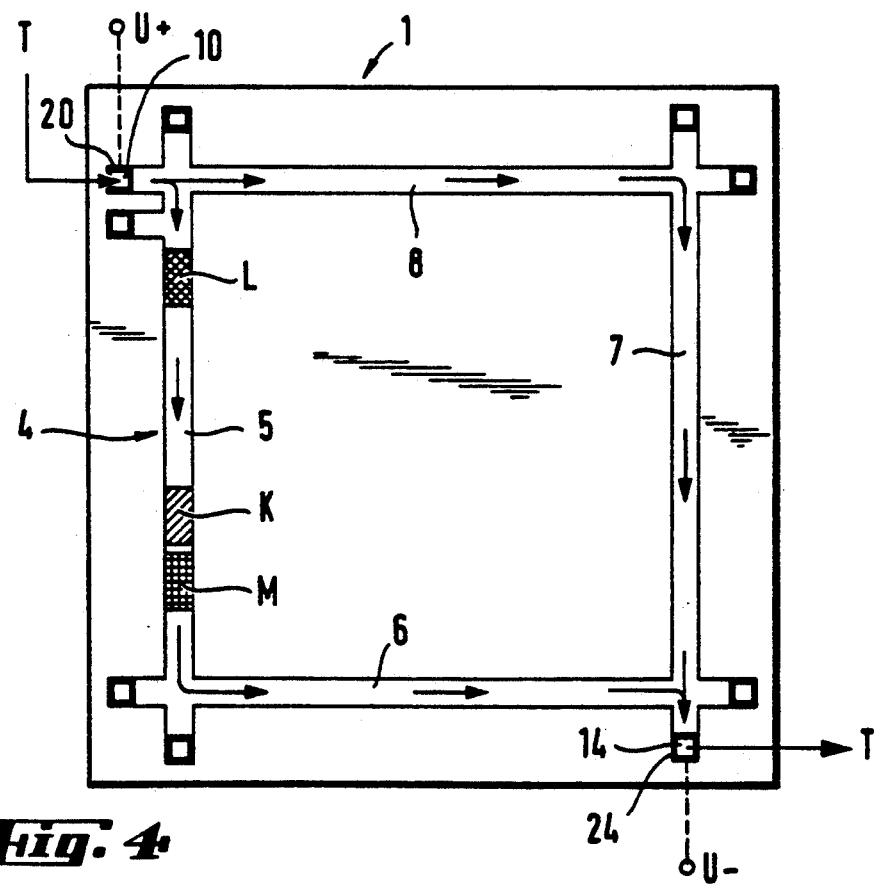

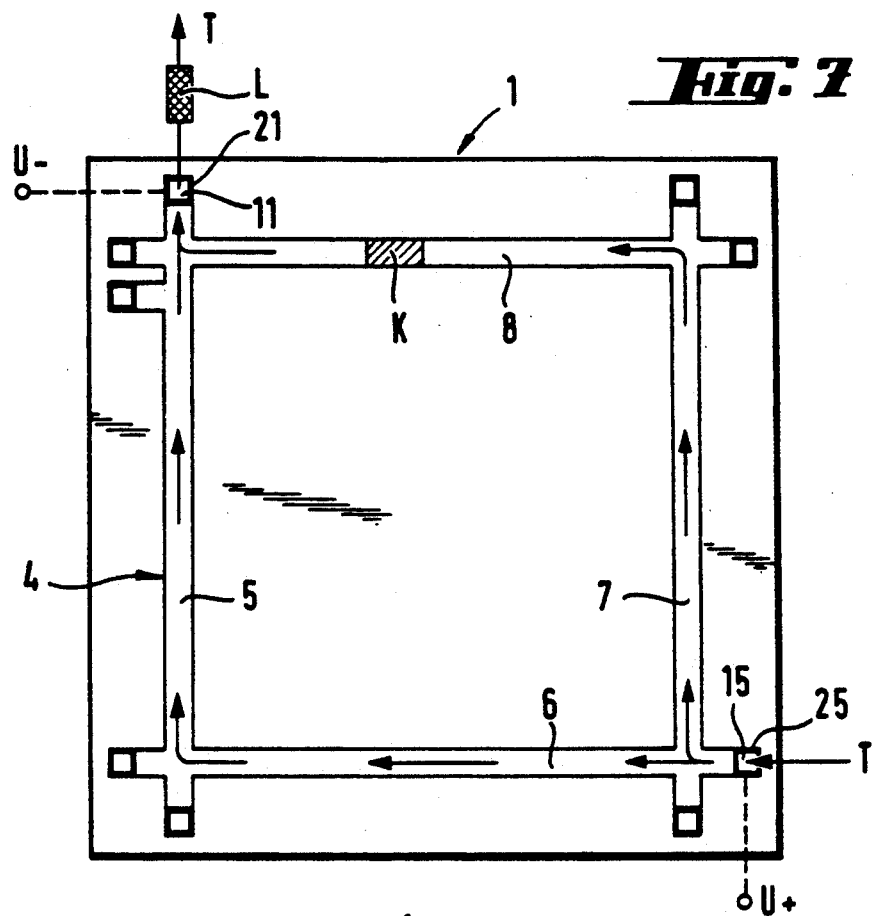
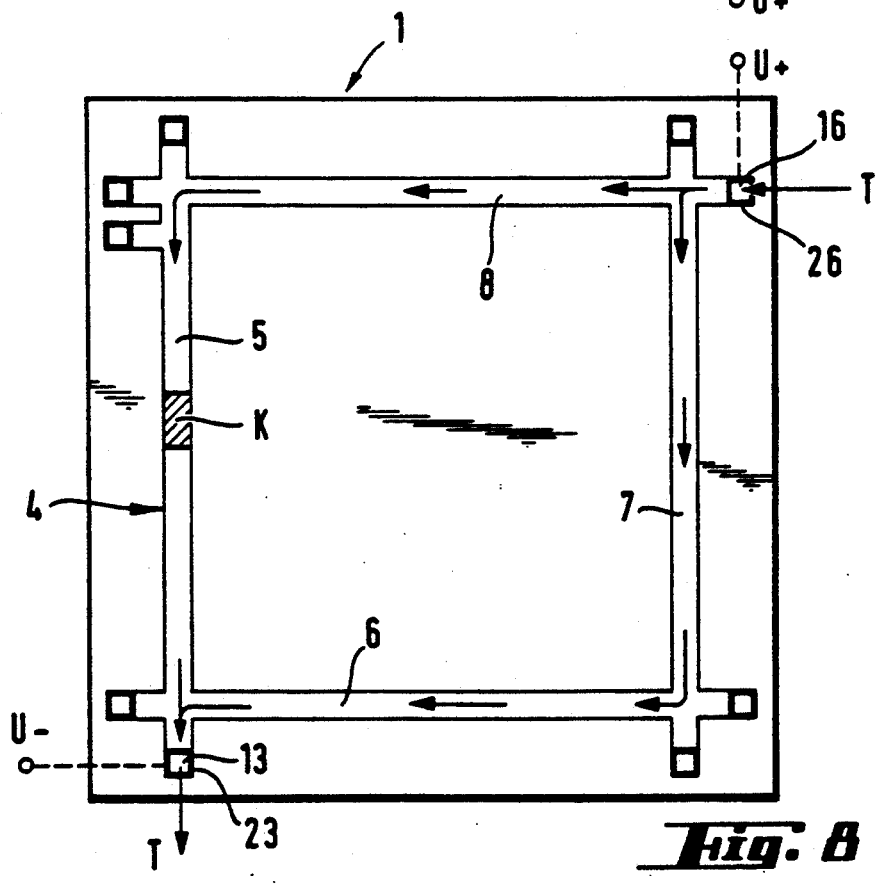

ELECTROPHORETIC SEPARATING DEVICE AND ELECTROPHORETIC SEPARATING METHOD

The invention relates to an electrophoretic separating device in accordance with the preamble of patent claim 1 and an electrophoretic separating method in accordance with the preamble of patent claim 15.

In the course of the automation of preparation processes and analysis methods, for example in analytical chemistry, process measuring technology, environmental analysis or medical diagnostics, increasing importance is being attached to automated separating methods and particularly electrophoretic separating methods. Electrophoretic separating methods are used for the separation of samples into their constituents for the purpose of analysis and also for the concentration of reaction products which may in turn be used by way of feedback loops, for example, for controlling the concentration of starting materials or additives, etc. The separating devices used usually operate continuously and are generally constructed in the form of so-called flow-injection analysis systems. Usually in such systems a carrier medium is transported through a capillary system into which a sample to be analysed or separated is injected at a suitable point. The transport of the media is in many cases effected using suitable pumps; it is also possible, however, to use suitable electrolytes as the carrier medium and to effect the transport by means of an electric field, thereby exploiting the electroosmotic effect.

The separation of the sample into its components is effected electrophoretically in an applied electric field. The electric field is an essential parameter for the separating performance of the device and is also crucial for the duration of the separating operation. To achieve good separation results it is desirable to have electric field strengths of 20 kV/m or more over the effective channel length. In order to reduce the time required for separation it is desirable to have relatively high field strengths. However, in electrophoresis using glass capillaries, which are usually 0.5–2 m in length, a limit of about 30–40 kV/m is given by the capillary material and the surrounding air. This results in separating times of about 30 minutes for one separating run. If it is not possible to separate all the components in one run, then the relevant portion of the sample is re-injected and a further separation is carried out, and so on. Since in may cases a large number of separating runs is necessary in order to separate all the components from one another, the total duration of the separating operation may be several hours or more.

An article by K. A. Ramsteiner in the Journal of Chromatography, 456 (1988) 3-20, pages 3-20, describes chromatographic analysis systems that make use of glass capillaries. In particular, networks of two or more glass columns interconnected by way of valves are described, and variants of the interconnection are mentioned. However, separating devices of such construction having glass capillaries often have internal dead spaces in the region of the connecting capillaries, injection valves or network valves etc., which can have a very disadvantageous effect on the separating performance of the device.

An article by M. Jansson et al. in the Journal of High Resolution Chromatography, 1989, pages 797-801, describes some essential aspects of electrophoretic separating methods, especially capillary electrophoresis. In the article it is also pointed out that there is a desire to miniaturise such electrophoretic separating systems and preferably to integrate them on silicon material. Silicon material is especially valued because of its good workability known from the semi-conductor industry.

U.S. Pat. No. 4,908,112 describes a miniaturised analysis device for biological investigations, and especially an electrophoretic separating device constructed on a silicon wafer. A meandering arrangement of the capillary channel enables the separating path to be lengthened within the confines of the limited dimensions of the silicon wafer.

Apart from the limits on the length of separating path, and thus on the separating results that can be achieved, imposed by the dimensions of the silicon wafer, the desire for a separating path that is as long as possible is in conflict with the desire for further miniaturisation of the electrophoretic separating device. Furthermore, a further very substantial problem in the integration of such capillary electrophoresis devices on silicon material, other semi-conductive materials or alternatively on glass, lies especially in the fact that the electric field strengths effective over the entire length of the channel are very limited. A decisive factor for the field strengths that can be used is the quality of the insulating layer between the carrier medium transported in the capillary channel and the semi-conductive material. The insulating layer is usually formed by a natural silicon oxide layer. It is also possible to reinforce this natural insulating layer by means of further, artificially applied insulating layers. Especially suitable for this purpose are, for example, the silicon nitride, tantalum silicide or further silicon oxide layers known from the semiconductor industry. It will be understood, however, that such insulating layers cannot be applied in any desired thickness. In addition, every such additional treatment step cannot be achieved without a large amount of technical outlay and will be associated with additional costs.

The problem therefore exists of eliminating these disadvantages of electrophoretic separating devices known from the prior art. An electrophoretic separating device should be provided that has a very high separating performance. At the same time the device should be capable of being further miniaturised and of being produced in an economical mass production process. An electrophoretic separating method should also be developed that enables complex analyses to be carried out, even with channel lengths that are limited per se, and in addition allows the sample for analysis or separation into its components to be exposed to high electric field strengths. Furthermore, the process should be quick to carry out and should produce high separating performances in a short time.

All these problems and other problems associated therewith are solved by an electrophoretic separating device in accordance with the latter part of patent claim 1 and by an electrophoretic separating method in accordance with the latter part of patent claim 15. Especially preferred embodiments of the device according to the invention and variants of the method according to the invention will be found in the respective associated dependent patent claims.

There is provided especially an electrophoretic separating device comprising a channel which is provided in the region of its ends with inlet and outlet openings, for example for a carrier medium, and which has at least one feed opening for a sample to be investigated, and having electrodes in the region of the inlet and outlet openings, which electrodes can be connected to a voltage source in such a manner that an electric field can be established along the channel. According to the invention the electrophoretic separating device is characterised in that the channel is constructed in the form of a closed loop. In this way, despite the limited dimensions of the device it is possible to obtain separating paths of any desired length which are dependent solely upon the number of circuits made by the sample to be separated in the closed channel. On each circuit the electric field strength "experienced" by the sample is added to that of the preceding circuits.

Preferably, the channel is constructed in the manner of a capillary.

In a preferred embodiment, the channel is divided into n channel sections and has, in addition to the feed opening for the sample, 2n inlet and outlet openings that are arranged in the region of connection between the channel sections.

It is especially advantageous if each channel section is associated with electrodes which can be connected to the voltage source in such a manner that the electric field can be applied substantially along the channel region that is arranged between the relevant electrodes which electrodes have different electrical potentials. The electrodes are generally not arranged directly in the channel region in question but are provided in the region of the inlet and outlet openings. By arranging the electrodes in the supply and collecting vessels for the carrier medium, which vessels are of open construction, it is possible to avoid the formation of bubbles in the channel region. With such a construction, the sample to be separated can be exposed to a considerably greater electric field. The potential difference compatible with the material used is applied only in a relevant portion of the channel. The total electric field strength applied along a circuit and acting on the sample to be separated corresponds to the sum of the field strengths acting on the sample in each of the portions. The total field strength to which a sample to be separated is exposed corresponds in turn to the field strength on one circuit multiplied by the number of circuits in the closed channel, so that the resulting field strength constitutes a multiple of the field strength being present in the respective portion of the channel.

It is also especially advantageous of the channel region to which the electric field is applied comprises at least two channel sections the connection region of which is associated with an electrode having a potential lying between the potentials of the source electrodes of the electric field.

The voltage source used is preferably a controllable direct voltage source. The electrodes are preferably connected to the voltage source in pairs with the aid of a relay so as to create an electric field that migrates cylically along the individual channel regions.

The channel is especially advantageously constructed in the form of an n-sided figure the sides of which are formed by the channel sections. In that case, the channel comprises at least three channel sections.

In a preferred embodiment, the electrophoretic separating device according to the invention is constructed in the form of a miniaturised component preferably comprising two parts which are constructed in the form of a body part and a lid part, preferably of glass, with the channel, the inlet and outlet openings and the feed opening preferably being provided on the body part.

When mass production techniques known from the semi-conductor industry are used, it is especially advantageous for the body part to be a preferably photolithographically or micromechanically machined plate of glass or of semi-conductive material, preferably a silicon plate.

If the electrophoretic separating device according to the invention is to be used for analysis purposes, it is especially advantageous if it comprises at least one detector, for example an absorption detector for ultraviolet radiation or for the visible spectrum, or a luminescence detector or an electrochemical detector, which is arranged along the channel.

The channel advantageously has a cross-sectional surface area of from approximately 100 $\mu m^2$ to approximately 5000 $\mu m^2$.

In the electrophoretic separating method according to the invention, a sample is introduced via a feed opening into an electrolytic carrier medium that is moved with the aid of an electric field through a channel that is provided in the region of its ends with inlet and outlet openings for the carrier medium, and is separated into individual components by the electric field which is generated in the channel by connecting electrodes in the region of the inlet and outlet openings to different potentials of a voltage source. The procedure for carrying out the method according to the invention is distinguished especially by the fact that the carrier medium and the sample are moved along a substantially closed path formed by the channel which is constructed in the form of a closed loop. In this manner it is possible to achieve for the sample to be separated virtually any length of separating path despite the limited dimensions of the separating device. This is achieved especially by moving the carrier medium and the sample repeatedly, especially cyclically, through the channel.

An especially advantageous feature of the procedure for carrying out the process according to the invention is that the electrical potential difference for generating the electric field for transporting the carrier medium and the sample is generated essentially only in a relevant portion of the channel, especially in that portion in which the sample is located, and, in accordance with the desired transport direction of the carrier medium and of the sample or the component of interest, the field is generated in successive portions. Although the maximum tolerable electric field strength is limited by the material used for the separating device, the sample to be separated can in this way be exposed to a considerably higher electric field strength, since the effects of the electric field in the portions are added together with the result that the sample receives in total a considerably greater electric field than has been applied in practice in any one channel region. In the course of the cyclic movement of the sample in the closed channel the electric field strength "suffered" during a circuit is multiplied by the number of circuits.

Preferably the switching frequency of the electrical potential difference to the adjacent channel region is matched to the circulation speed of the component of interest in the channel.

Especially for the purpose of concentrating a component of interest, the components that migrate more quickly or more slowly than the switching frequency are preferably discharged through the outlet openings arranged along the channel.

It is advantageous if the carrier medium and the sample or the component in each channel region are moved through at least two channel sections which each comprise at least one inlet and outlet opening and also comprise electrodes which are provided in the region of each opening and are connected to a voltage source.

It is especially advantageous if the electrodes provided at the beginning and end points of each channel region for generating the electric field are connected in pairs to a direct voltage source, while the electrode(s) located therebetween is(are) physically separated from the voltage source. This form of electrode control is especially advantageous when the carrier medium and the sample are moved along a channel that is constructed in the form of an n-sided figure and that is provided with 2n inlet and outlet openings in addition to the feed opening for the sample.

Advantageously, the electrical potential difference is switched on to the adjacent channel region only after the sample has been moved into the first channel section of the adjacent channel region.

Especially advantageously the channel is constructed in the manner of a capillary with a cross-sectional surface area of from approximately 100 $\mu m^2$ to approximately 5000 $\mu m^2$, the strength of the electric field being matched to the dimensions of the channel in such a manner that at a theoretical channel length of 1 m, the thermal heat output does not exceed 1 W.

Advantageously, when the microstructures are constructed in semi-conductive material, especially in silicon, the potential difference selected for generating the electric field is about 100 V–500 V. In this manner it is possible to avoid breakdown of the insulator layer of the separating device. If the microstructures are constructed in insulator material, for example in glass, it is possible to apply potential differences of up to several kilovolts, for example up to 5 kV.

It is also very advantageous to examine the state of separation of the sample into the individual components at least once per circuit in the channel with the aid of one or more detectors arranged along the channel.

The electrophoretic separating device according to the invention and the electrophoretic separating method according to the invention are described in more detail below with reference to the drawings which are in diagrammatic form.

BRIEF DESCRIPTION OF THE DRAWINGS

FIGS. 3–8 show the separating device according to FIG. 1 in six different states for the purpose of illustrating the electrophoretic separating method according to the invention.

Figure 2:
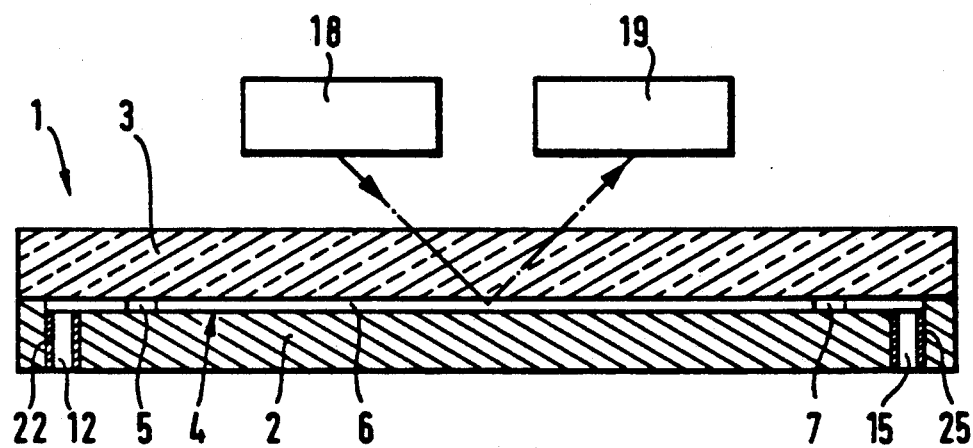
FIG. 2 is a section along line A—A in FIG. 1.

In the Figures, an embodiment of the electrophoretic separating device is indicated as a whole by the reference numeral 1. As can be seen from FIG. 2, the separating device is, for example, of two-part construction and comprises a body part 2 and a lid part 3. The embodiment shown is especially a miniaturised component. The lid part 3 is manufactured, for example, of glass, whereas the body part 2 consists, for example, likewise of glass or of a semi-conductive material, preferably of monocrystalline silicon. Glass or semi-conductive materials are therefore preferred as materials because of the wealth of experience that has been gained in the semi-conductor industry as regards the processing thereof using mass production techniques. Such materials can be processed using the most modern photolithographic or micromechanical techniques known from the manufacture of semi-conductors.

Figure 1:
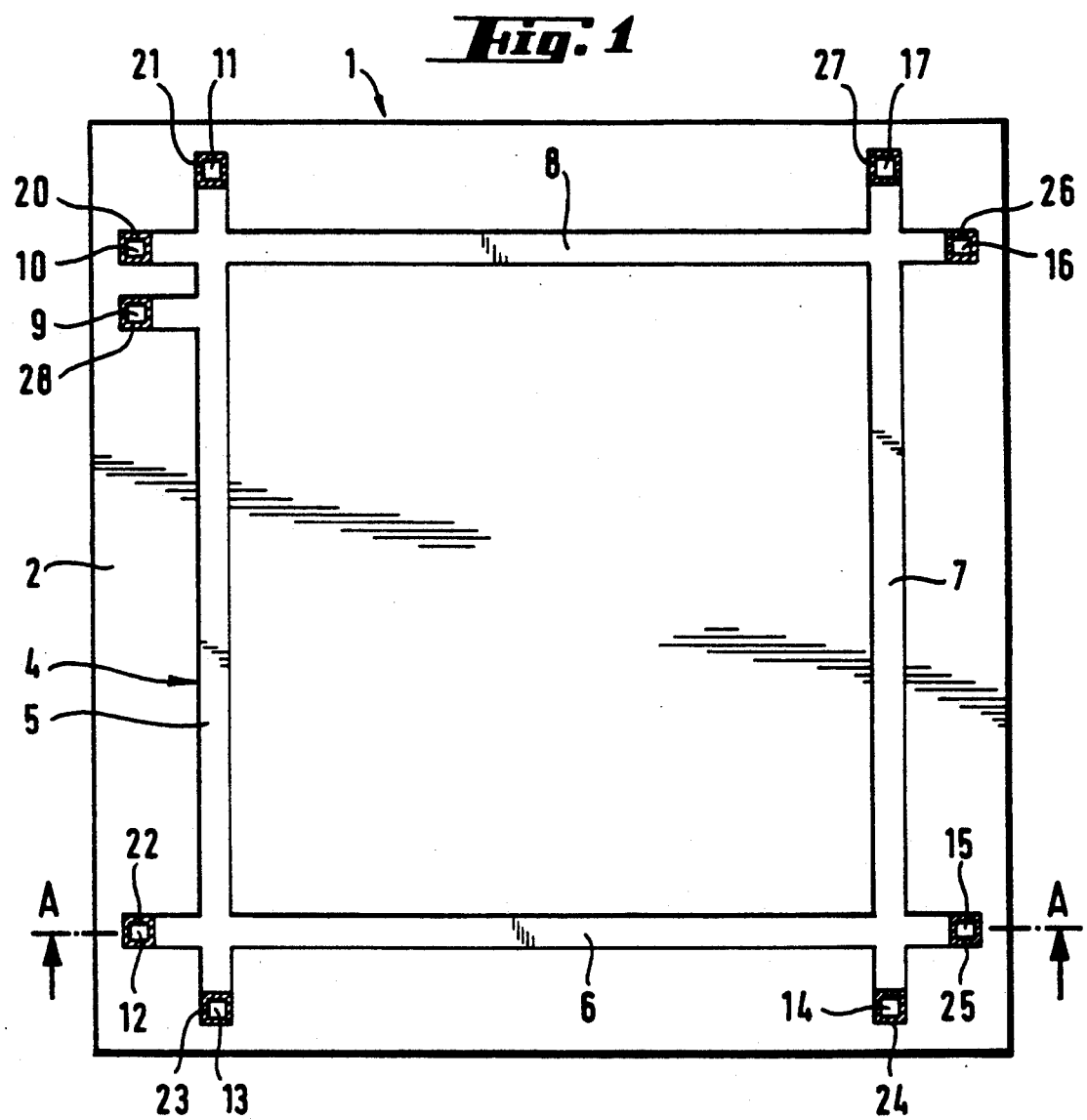
FIG. 1 is an embodiment of the electrophoretic separating device.

The body part 2 is shown in FIG. 1. It comprises a channel 4 which is provided with inlet and outlet openings 10–17 for a carrier medium. In addition to the inlet and outlet openings 10–17, the channel 4 has a feed opening 9 for a sample to be analysed or separated, which opening is constructed in the form of an insertion opening for a connection capillary (not shown). That connection capillary for the sample to be investigated preferably opens into a sample reservoir (not shown in the Figures for the sake of clarity). As can be seen very clearly in FIG. 1, the channel is constructed in the form of a closed loop. In a preferred embodiment the channel 4 is divided into n channel sections 5–8. In that case, in addition to having the feed opening 9 for the sample, the channel 4 is preferably provided with 2n inlet and outlet openings 10–17 for the carrier medium, which openings are each arranged in the region of connection between the individual channel sections 5–8 and are all preferably constructed in the form of attachment openings for connection capillaries. Those connection capillaries open into supply or collecting containers for the pure carrier medium or for the carrier medium contaminated with the sample or with components of the sample. For reasons of clarity the supply and collecting containers are not shown in the Figures. According to the embodiment of the separating device according to the invention shown in the Figures the feed opening 9 and the inlet and outlet openings 10–17 are constructed in the form of vertical through openings in the body part 2 which have been produced, for example, photolithographically. It will be understood that it is also possible to use other manufacturing techniques, for example the through openings can also be produced with the aid of a laser or the like, particularly in the case of other materials.

In the view shown in FIG. 1, the channel 4 constructed in the form of a closed loop has the shape of a four-sided figure, but it may be constructed quite generally in the form of an n-sided figure or alternatively may have approximately the shape of a circle. When constructed in the form of a general n-sided figure, the number of sides is preferably at least three. The sides of the n-sided figure are formed by the channel sections 5–8.

In the region of the inlet and outlet openings 10–17 there are provided electrodes 20–27 that can be connected to a voltage source (not shown) in such a manner that an electric field can be established along the channel 4. In FIG. 1 the electrodes 20–27 are shown by hatched areas in the region of the inlet and outlet openings 10–17. An electrode 28 is indicated in the region of the feed opening 9 for the sample to be separated. The electrodes can be provided, for example, by metallising the inner sides of the through openings and connections can be made to them from the outside. They can, however, also be constructed in the form of electrodes (not shown) that extend vertically with respect to the channel 4 in the region of the inlet and outlet openings 10–17 and that are connected to contact surfaces on the body part 2. Connecting wires can be attached (bonded) to the contact surfaces and can be guided to the outside through the separating device which is constructed in the form of an analysis chip in the manner of, for example, a memory chip. An arrangement of the electrodes in the supply and collecting containers for the carrier medium, which containers are connected to the inlet and outlet openings of the separating device and are preferably of open construction, helps to prevent the formation of bubbles in the respective channel region.

It is especially advantageous if each channel section 5-8 is associated with electrodes 20-27 which can be connected to the voltage source (not shown) in such a manner that the electric field can be applied along the channel region that is arranged between the relevant electrodes which electrodes have different electrical potentials. With such a construction, the sample to be separated can be exposed to a considerably greater electric field. The potential difference compatible with the material used is at any given time applied only in a portion of the channel 4. The total electric field strength acting on the sample to be separated along a circuit corresponds to the sum of the field strengths acting on the sample in each of the portions. The total field strength to which a sample to be separated is exposed corresponds in turn to the field strength on one circuit multiplied by the number of circuits in the closed channel, so that the resulting field strength constitutes a multiple of the field strength being present in the respective portion of the channel. It is advantageous to combine at least two, preferably three, channel sections to form each channel region. The electric field is then effective in the entire channel region. The source electrodes arranged at the beginning and at the end of the respective channel region are connected to the potential terminals of the voltage source. The electrodes arranged in the region of connection between the channel sections have in this case a potential lying between the potentials of the source electrodes of the channel region.

Preferably the electrodes in the regions of connection between the channel sections of a channel region in which the electric field is present are separated physically from the voltage source so that they can float freely and set themselves at any potential between the potentials of the respective two source electrodes. This embodiment is advantageous especially when there is used a direct voltage source to which the electrodes are connected via a relay. As a result of the paired connection of the source electrodes of one channel region to the potential terminals of the direct voltage source there is generated a field that migrates cyclically along the individual channel regions. Instead of a direct voltage source the electrodes may also be connected to alternating voltage sources. Depending upon the desired circulation direction of the sample in the channel, the alternating voltages that are applied to the successive electrodes 20-27 along the channel 4 must be correspondingly out of phase. The frequency of the alternating voltages is dependent upon the component of interest, which should of course remain in the channel 4 to the end.

The channel 4 of the electrophoretic separating device 1 is preferably constructed in the manner of a capillary. The channel 4 is usually created using photolithographic or micro-mechanical processing techniques in which there is formed in the body part 2 a trough the cross-sectional shape of which depends to a great extent upon the chosen production technique, for example wet chemical etching, plasma etching or isotropic etching. The open side of the trough forming the channel 4 is covered by the lid part 3. Advantageously the channel 4 has a cross-sectional surface area of from approximately 100 $\mu m^2$ to approximately 5000 $\mu m^2$.

If the electrophoretic separating device 1 according to the invention is to be used for analysis purposes it is especially advantageous if it comprises at least one detector 18, 19, for example an absorption detector for ultraviolet radiation or for the visible spectrum, or a luminescence detector or an electrochemical detector, which is arranged along the channel. In accordance with the view shown in FIG. 2, the detector is constructed, for example, in the form of an absorption detector and comprises a light source 18 and a photosensitive detector cell 19, both of which are arranged above the transparent glass lid part 3. The detector can, however, also be integrated on the body part 2 and arranged in a portion of the channel 4. Especially the construction of the body part 2 in semi-conductive material, for example in monocrystalline silicon, and the use of manufacturing techniques known from the semi-conductor industry, enable electronic detector elements to be integrated directly on the silicon plate. In this manner there is formed an analysis chip which not only comprises "mechanical" elements, such as channels and branches or connection openings, but also can be equipped with electronic circuits. The surface area of the analysis chip is preferably from approximately 20 $mm^2$ to approximately 500 $mm^2$.

In the following, the electrophoretic separating method according to the invention will be described in more detail with reference to FIGS. 3-8. The components and elements of the electrophoretic separating device 1 have been given the same reference numerals as in FIGS. 1 and 2. As shown in FIG. 3, a carrier medium T, usually an electrolyte, is introduced, for example via the inlet opening 10, into the channel 4 which is constructed in the form of a closed loop. This operation is carried out, for example, by means of connection capillaries which open into a supply container for the carrier medium. The transport can be effected by means of micropumps but it is also possible to use electric fields for the transport, in which case it should be taken into consideration that the carrier medium is generally transported from the more positive to the more negative potential.

In the first stage of the electrophoretic separating method according to the invention, which is shown in FIG. 3, the potential difference of a direct voltage source has been applied, for example, between the electrode 20 at the inlet opening 10 and the electrode 24 at the outlet opening 14. The electrodes in the region of connection between the channel sections 5 and 6 are, for example, not connected to the voltage source and are able to set themselves at a potential lying between the potentials of the source electrodes 10 and 14 connected to the potential terminals of the voltage source. This results in an electric field that extends both over the channel region formed by channel sections 5 and 6 and over the channel region formed by channel sections 7 and 8. The carrier medium is in each case transported from the inlet opening 10 to the outlet opening 14. The outlet opening is connected, for example via a connection capillary, to a collecting container for the carrier medium T.

Figure 5:
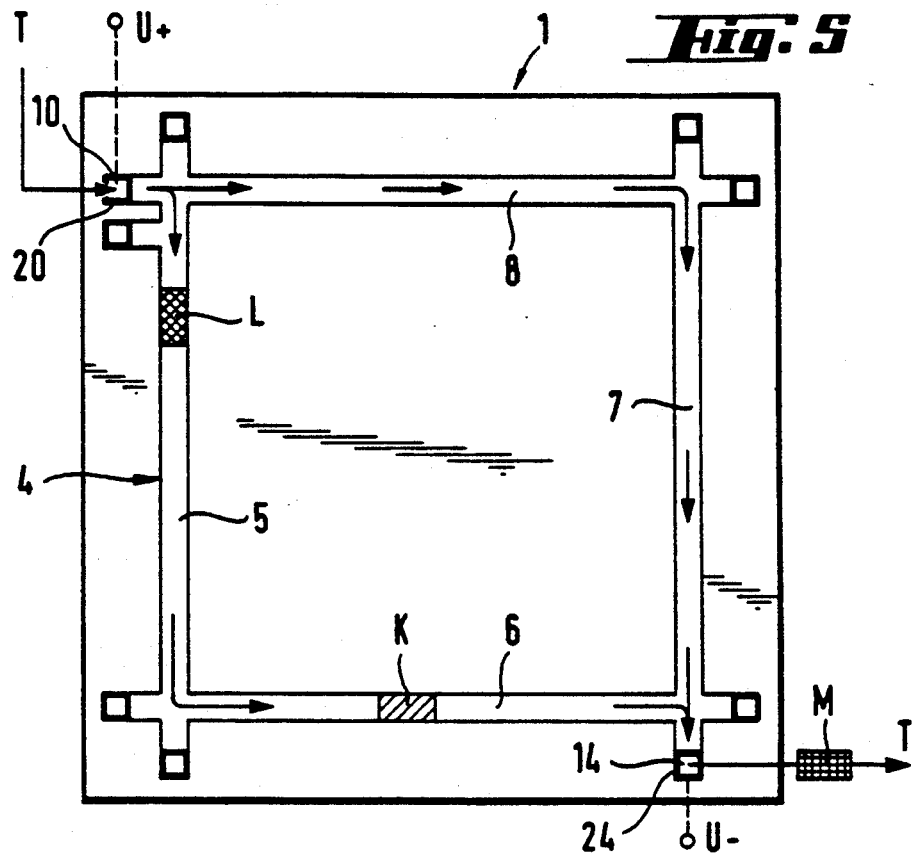
Figure 6:
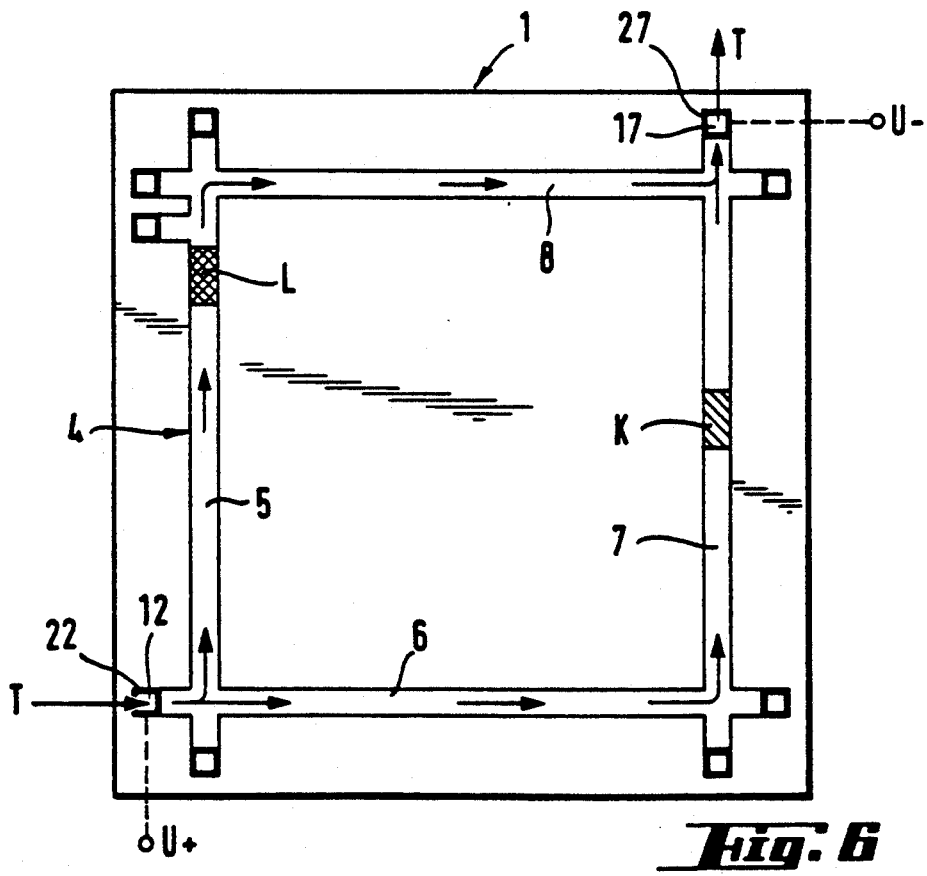

A sample P, which in the example shown comprises components K, L and M, is introduced via the feed opening 9. Along their transport path the components K, L and M are separated in accordance with their migration speeds in the applied electric field. This is shown in FIGS. 4 and 5. Component M, which has the highest migration speed in the electric field, is finally discharged together with the carrier medium T through the outlet opening 14, so that only components K and L remain in the channel. Component M is supplied together with the carrier medium T to a collecting container.

Before the component K of interest is likewise discharged through the outlet opening 14, the electrical potential difference is switched to the electrodes 22 and 27 bordering the next channel region 6,7. In accordance with FIG. 6, the source electrodes 22 and 27 are arranged at the ends of the channel region in the region of the inlet and outlet openings 12 and 17, respectively. The inlet opening 12 is connected to a supply container for the carrier medium T so that a continuous supply of fresh carrier medium can be provided, and the outlet opening 27 is connected to a collecting container. The polarity of the electric field in the channel 4 is so chosen that the component of interest K is transported on into channel section 7, while component L in channel section 5 is transported back to the outlet opening 21.

Shortly before the component K of interest is discharged through the outlet opening 17, the potential difference is switched on to the electrodes 25 and 21 bordering the next channel section 7,8. As a result, component K is moved further in channel section 8, while component L is discharged together with the carrier fluid T through the outlet opening 11 into a collecting container.

By again switching over the potential difference to the electrodes 26 and 23 bordering the subsequent channel region 8,5, the component K of interest is moved into channel section 5.

It will be understood that the separation of the sample P into its components K, L and M will generally not be accomplished after only one circuit. Many circuits are usually necessary to carry out such a separation. Because the channel 4 is constructed in the form of a closed loop it is possible to achieve virtually any length of separating path, since the sample can be moved cyclically through the channel. The lengths of separating path that are possible are limited only by the diffusion behaviour of a particular sample in a particular carrier medium. The switching frequency of the potential difference to the electrodes in the respective adjacent channel regions is preferably matched to the circulation speed of the component K of interest in the sample P. The switching frequency is generally derived from the time necessary for one circulation of the components divided by the number of channel regions. In this way all components that migrate more slowly or more quickly than the switching frequency are preferably discharged through the outlet openings arranged along the channel 4.

As a result of the fact that the electrical potential difference is only ever applied to a portion of the channel 4 through which the sample is being moved, and that the effects of the electric field caused by the potential difference are added together in each portion and on each circuit, the sample is in total exposed to an electric field that is a multiple of that actually corresponding to the potential difference in a particular channel region. Although the maximum tolerable potential difference or the electric field resulting therefrom is limited by the material used for the electrophoretic separating device, the separating performance can in this way be markedly increased. The strength of the electric field is matched to the dimensions of the channel, care being taken especially that at a theoretical channel length of 1 m, the thermal heat output in the channel does not exceed 1 W. When the body parts are made of semiconductive silicon, the potential differences chosen for this purpose are advantageously from approximately 100 V to approximately 500 V. In this way it is possible to avoid electrical breakdown of the insulator layer of the separating device. If the body parts are made of insulator material, for example of glass, potential differences of up to several kilovolts, for example up to 5 kV, can be applied without producing electrical breakdown.

Separation can be carried out particularly advantageously and efficiently if the sample or the more or less separated components is (are) moved past one or more detectors distributed along the channel 4 at least once per circuit. In this way the degree of separation of the sample or the degree of concentration of a component of the sample can be readily monitored. Furthermore, in this way the separating process can also easily be automated.

The electrophoretic separating device according to the invention and the electrophoretic separating method according to the invention overcome the disadvantages of the prior art. Very high separating performances can be achieved. Because it is possible to expose the sample to be separated to electric field strengths that are very high in total, the time required for separation into the individual components is markedly reduced. For example, depending upon the sample to be separated, the time taken for one circuit in the channel is, for example, only about 2-10 seconds. If the migration speed of the component of interest in the sample is assumed to be about 2.5-5 mm/s and the channel length per circuit about 8-40 mm, then in a separating period of about 1-30 minutes there are obtained separating performances in the order from 100 000 up to 1 000 000 separating stages (theoretical plates) or more. The separating device according to the invention can be manufactured economically and reproducibly in large numbers using mass production techniques, especially using manufacturing techniques known from the semi-conductor industry.

What is claimed is:

1. An electrophoretic separating device comprising a channel which is provided with inlet and outlet openings, for example for a carrier medium, and which has at least one feed opening for a sample to be investigated, and having electrodes in the region of the inlet and outlet openings, which electrodes can be connected to a voltage source in such a manner than an electric field can be established along the channel, wherein the channel is divided into n channel sections and has, in addition to the feed opening for the sample, 2n inlet and outlet openings that are arranged in the region of connection between the channel sections, and wherein the channel is constructed in the form of an n-sided closed loop figure, the sides of which are formed by the channel sections.

2. A device according to claim 1, wherein the channel is constructed in the manner of a capillary.

3. A device according to claim 1, wherein each channel section is associated with electrodes which can be connected to the voltage source in such a manner that the electric field can be applied substantially along a channel region that is arranged between the relevant electrodes, which electrodes have different electrical potentials.

4. A device according to claim 3, wherein the channel region along which the electric field is applied comprises at least two channel sections the connection region of which is associated with an electrode having a potential lying between the potentials of the source electrodes of the electric field.

5. A device according to claim 4, wherein the voltage source is a direct voltage source.

6. A device according to claim 5, wherein the electrodes can be connected to the voltage source in pairs, preferably with the aid of a relay, so as to generate an electric field that migrates cyclically along the individual channel regions.

7. A device according to claim 1, wherein the channel comprises at least three channel sections.

8. A device according to claim 1, which is constructed in the form of a miniaturised component which is preferably of two-part construction and comprises a body part and a lid part, preferably of glass, with the channel, the inlet and outlet openings and the feed opening preferably being provided on the body part.

9. A device according to claim 8, wherein the body part is a micromechanically or photolithographically machined glass plate.

10. A device according to claim 8, wherein the body part is a preferably photolithographically or micromechanically machined plate of semi-conductive material, preferably a silicon plate.

11. A device according to claim 1, which comprises at least one detector, for example an absorption detector for ultraviolet radiation or for the visible spectrum, or a luminescence detector or an electrochemical detector, which is arranged along the channel.

12. A device according to claim 1, wherein the channel has a cross-sectional surface area of from approximately 100 $\mu m^2$ to approximately 5000 $\mu m^2$.

13. An electrophoretic separating method wherein a sample is introduced via a feed opening into an electrolytic carrier medium that is moved with the aid of an electric field through a channel being provided with inlet and outlet openings for the carrier medium, and is separated into individual components by the electric field which is generated in the channel by connecting electrodes in the region of the inlet and outlet openings to different potentials of a voltage source, which method comprises moving the carrier medium and the sample along a substantially closed path formed by the channel which is constructed in the form of an n-sided closed loop figure and that is provided with 2n inlet and outlet openings in addition to the feed opening for the sample.

14. A method according to claim 13, wherein the carrier medium and the sample are moved repeatedly, especially cyclically, through the channel.

15. A method according to claim 13, wherein the electrical potential difference for generating the electric field for transporting the carrier medium and the sample is generated essentially only in a relevant portion of the channel, especially in that portion in which the sample is located, and, in accordance with the desired transport direction of the carrier medium and of the sample or the component of interest, the field is generated in successive portions.

16. A method according to claim 15, wherein the switching frequency of the electrical potential difference to the adjacent channel regions is matched to the circulation speed of the component of interest in the channel.

17. A method according to claim 16, wherein the components that migrate more quickly or more slowly than the switching frequency are discharged through the outlet openings arranged along the channel.

18. A method according to claim 16, wherein the carrier medium and the sample or the component of interest in each channel region are moved through at least two channel sections which each comprise at least one inlet and outlet opening and also comprise electrodes which are provided in the region of each opening and are connected to a voltage source.

19. A method according to claim 18, wherein the electrodes provided at the beginning and end points of each channel region for generating the electric field are connected in pairs to a direct voltage source and the electrode(s) located therebetween is(are) physically separated from the voltage source.

20. A method according to claim 13, wherein the electrical potential difference is switched on to the adjacent channel region only after the sample has been moved into the first channel section of the adjacent channel region.

21. A method according to claim 13, wherein the channel is constructed in the manner of a capillary and with a cross-sectional surface area of from approximately 100 $\mu m^2$ to approximately 5000 $\mu m^2$, and the strength of the electric field is matched to the dimensions of the channel in such a manner that at a theoretical channel length of 1 m, the thermal heat output does not exceed 1 W.

22. A method according to claim 21, wherein the potential difference selected for generating the electric field is from approximately 100 V to several kilovolts, in the case of a semi-conductive material preferably up to about 500 V.

23. A method according to claim 13, wherein the state of separation of the sample into the individual components is examined at least once per circuit in the channel with the aid of one or more detectors arranged along the channel.

* * * * *